(12) United States Patent
Barrasa Shaw et al.

(10) Patent No.: US 11,523,827 B2
(45) Date of Patent: Dec. 13, 2022

(54) PURSE SUTURING DEVICE FOR HOLLOW VISCUS

(71) Applicants: Antonio Barrasa Shaw, Valencia (ES); Alberto Gimenez Sancho, Valencia (ES)

(72) Inventors: Antonio Barrasa Shaw, Valencia (ES); Alberto Gimenez Sancho, Valencia (ES)

(73) Assignees: Antonio Barrasa Shaw, Valencia (ES); Alberto Gimenez Sancho, Valencia (ES)

( * ) Notice: Subject to any disclaimer, the term of this patent is extended or adjusted under 35 U.S.C. 154(b) by 772 days.

(21) Appl. No.: 16/514,220

(22) Filed: Jul. 17, 2019

(65) Prior Publication Data
US 2020/0022704 A1  Jan. 23, 2020

(30) Foreign Application Priority Data

Jul. 19, 2018  (ES) .............................. ES201831153U

(51) Int. Cl.
| *A61B 17/11* | (2006.01) |
| *A61B 17/115* | (2006.01) |
| *A61B 17/04* | (2006.01) |
| A61B 17/00 | (2006.01) |

(52) U.S. Cl.
CPC ...... *A61B 17/1114* (2013.01); *A61B 17/0467* (2013.01); *A61B 17/0469* (2013.01); *A61B 17/1155* (2013.01); A61B 2017/00818 (2013.01); A61B 2017/00955 (2013.01); A61B 2017/0496 (2013.01); A61B 2017/1132 (2013.01); A61B 2017/1135 (2013.01); A61B 2017/1142 (2013.01)

(58) Field of Classification Search
CPC ............... A61B 17/1114; A61B 17/115; A61B 17/1155; A61B 2017/1132; A61B 2017/1142; A61B 2017/00818; A61B 17/12; A61B 17/0469; A61B 2017/1135
See application file for complete search history.

(56) References Cited

U.S. PATENT DOCUMENTS

| 4,304,236 | A | * | 12/1981 | Conta | .................. | A61B 17/115 |
| | | | | | | 227/19 |
| 6,543,456 | B1 | * | 4/2003 | Freeman | ............... | A61F 5/0083 |
| | | | | | | 128/898 |
| 2006/0085036 | A1 | * | 4/2006 | Viola | ............... | A61B 17/00491 |
| | | | | | | 606/228 |
| 2013/0032628 | A1 | * | 2/2013 | Li | ...................... | A61B 17/0293 |
| | | | | | | 600/249 |

* cited by examiner

*Primary Examiner* — Diane D Yabut
*Assistant Examiner* — Christina C Lauer
(74) *Attorney, Agent, or Firm* — Lucas & Mercante LLP

(57) ABSTRACT

A purse suturing device includes a circular stapler having a tubular stapler head adapted to be inserted inside a section of the hollow viscus to be sutured, a handle with an actuator connected to the stapler head, and an anvil against which the staples may be folded. The anvil has a pole adapted to be inserted into the tubular stapler head. A suturing thread is wound around the hollow viscus and tightened, causing a section of the hollow viscus to be tightened around the pole. The tightened section also includes a pursed, or folded, section of the wall of the hollow viscus, in which two layers of the wall of the hollow viscus are stapled together.

3 Claims, 23 Drawing Sheets

PURSE SUTURING DEVICE FOR HOLLOW VISCUS

CROSS REFERENCE TO RELATED APPLICATION

This application claims the benefit of Spanish Patent Application No. U 201831153, filed Jul. 19, 2018, which is incorporated herein by reference.

TECHNICAL FIELD

The present disclosure relates to the field of surgical devices, and more particularly to devices for performing surgery related to hollow viscera, such as anastomosis.

BACKGROUND

An anastomosis is a union of two hollow viscera created by surgeons to restore the transit of the contents when a part of the viscus is removed (for instance, when cutting part of or the whole colon to remove a cancer).

An anastomosis can be side-to-side (joining the side of one of the parts to the side of the other part), end-to-end (joining the end of one of the parts to the end of the other part), or end-to-side (joining the end of one of the parts to the side of the other part). An anastomosis can also be classified as hand-sewn or mechanical. A mechanical anastomosis is formed by use of a stapler. FIGS. 1a-1c show different types of hand-sewn anastomoses. FIG. 1a shows an end-to-end anastomosis. FIG. 1b shows and side-to-side anastomosis. FIG. 1c shows an end-to-side anastomosis.

In some hollow viscera, any type of anastomosis may work. However, in certain cases, mechanical end-to-end or end-to-side anastomoses are preferred. This is the case for esophageal and low rectal surgeries, for example. FIG. 2 shows how a mechanical low rectal anastomosis is performed using a circular stapler. FIG. 3 shows two conventional circular staplers for esophageal and rectal anastomosis.

As illustrated by FIGS. 2 and 3, conventional circular staplers have two detachable parts: a case, and an anvil on which staples may be folded to fix the tissues and secure the anastomosis. The case typically has a handle to operate the device, a stapler head containing several concentric lines of staples (generally two or three concentric lines), a circular blade, which is concentric and interior to the lines of staples, and a central mater to which the anvil is attached, as shown in FIG. 3.

Referring to FIG. 2, the ends of both hollow viscera must be closed before an anastomosis is performed. FIG. 2 shows that for the colon; where there is plenty of space, a purse suture around the mater is preferred. This purse suture provides a better vascularized edge for the subsequent anastomosis. Instead, as shown in FIG. 2, the rectal stump is closed by means of a linear stapler. Then, this closure is perforated by the mater in the stapler head. This method of closing the rectal stump is an alternative that may need to be performed due to the difficult access to the rectum in the pelvis. However, this method is not free of drawbacks and risks that are of significant concern to surgeons. Two of the most significant drawbacks are the need for multiple firings of the linear stapler to close the rectal stump, and the high possibility of leaving part of the closing suture outside the area covered by the circular stapler. Both of these possibilities occur frequently and create low vascularized areas that can lead to a dehiscence of the anastomosis, which can threaten the patient's life.

Several alternative methods for performing an anastomosis have been developed recently. For instance, a trans-anal approach to perform a hand-sewn purse suture. However, this option is technically difficult and can only be performed by a surgeon who has undergone significant training.

Another alternative method uses a device known as the "purse-string" which combines a thread, and a linear suturing device that fixes the thread to the hollow viscera. The thread is fixed with staples that are stuck to the wall of the viscus, one leg each side of the thread. This device has several drawbacks. For example, the device is not available for laparoscopic surgery due to its shape. The device is unable to reach difficult spaces such as the low rectum. Finally, since the staples cannot be curved, the fixation is weak and the staples detach due to movements of the viscera or the thread.

Accordingly, there is a need for an improved device for performing anastomoses. For example, there is a need for an improved device which provides an efficient suture or closing of the ends of hollow viscera before an anastomosis is performed.

SUMMARY

In accordance with an embodiment, a purse suturing device for hollow viscus is provided. In one embodiment, the device includes a circular stapler and a suturing thread.

In accordance with an embodiment, the device may be used to perform a purse suture at a hollow viscus. For example, the device may be used to prepare a mechanic end-to-end anastomosis or a side-to-end circular anastomosis. In this case, the function of this purse-suturing device is mainly preparing one end of the hollow viscus to be sutured to another end by means of a conventional circular stapler. The purpose is to create a purse suture in a mechanical way, in some parts of the body where a hand-sewn purse suture is not possible or is very difficult, as in the case of the lower rectum or the oesophagus.

In accordance with an embodiment, a purse suturing device includes a circular stapler and a suturing thread. The circular stapler has a tubular stapler head adapted to be inserted inside a section of the hollow viscus to be sutured, a handle with an actuator connected to the stapler head, and an anvil against which the staples may be folded. The anvil has a pole adapted to be inserted into the tubular stapler head. In one embodiment, the suturing thread is wound around the hollow viscus and tightened, causing a section of the hollow viscus to be tightened around the pole. The tightened section of the hollow viscus has a reduced radius. The tightened section also includes a pursed, or folded, section of the wall of the hollow viscus, in which two layers of the wall of the hollow viscus are prepared to be stapled together.

In accordance with an embodiment, the circular stapler has a first, pursing position in which the thread is wound around the hollow viscus, tightening the thread and pursing the wall of the hollow viscus around the tightened thread, and a second, stapling position in which the pursed wall of the hollow viscus is compressed and folded between the anvil and the stapler head. When the circular stapler is in the second, stapling position, the actuator actuates the stapler head, and a plurality of staples are pressed through the two folded layers of the pursed wall of the hollow viscus. The folded staples are fixed in place to secure the folded layers of the hollow viscus in their pursed position and thus complete a purse suturing of the hollow viscus.

In accordance with an embodiment, a purse suturing device includes a new circular suturing device or circular stapler, and a suturing thread, such that, the circular stapler along with the suturing thread, performs a purse suture at a hollow viscus. The purse suture can be used, for example, to prepare mechanic end-to-end or side-to-end circular anastomosis.

In accordance with an embodiment, the circular stapler has a tubular case configured to be inserted inside a section of the hollow viscus, a tubular stapler head placed in the interior of the tubular case and configured to be displaced concentrically along the interior of the tubular case and to push staples, which comprises a staple carrier, a handle comprising an actuator connected to the stapler head, and an anvil against which staples are folded.

In accordance with an embodiment, the suturing thread is configured to be wound around the hollow viscus closing it against the pole of the anvil and pursing the wall of the hollow viscus.

The anvil has a pole configured to be displaced concentrically along the interior of the stapler head. The pole of the anvil is configured to be displaced between a pursing position and a stapling position of the circular stapler.

In the pursing position of the circular stapler, the anvil is retracted from the staple carrier, creating between the anvil and the staple carrier a space that allows the thread to be wound around the hollow viscus, tightening a region of the hollow viscus against the pole of the anvil, and pursing the wall of the hollow viscus.

In the stapling position of the circular stapler, the anvil is moved to a position proximate to, or in contact with, the staple carrier, such the pursed wall of the hollow viscus is compressed and folded between the anvil and the staple carrier.

The dimensions of the circular stapler may vary according to the dimensions of the hollow viscus in which it is inserted.

The thread may comprise any suitable material and may have any suitable size. Accordingly, the thread may be made from different materials and have different sizes depending on various factors relating to, for example, the manufacturing and use of the circular stapler. In one embodiment, the thread comprises a plastic monofilament such as polypropylene.

According to an embodiment, the staple carrier of the stapler head has a plurality of projections which hold the staples in such a way that they are spaced from each other. Thus, the staple carrier includes a plurality of projections and a plurality of recesses to provide space for a stick to push the thread tight around the pole, avoiding the need to knot the thread. In this manner, the purse suture can be opened and closed as desired, for example, to allow the removal of the affected part of the hollow viscus through the pursed part of said hollow viscus, avoiding the need for an extra incision in the patient.

According to another embodiment, this circular stapler is attachable to a conventional circular stapler.

According to an embodiment, the anvil has a plurality of grooves against which staples are folded.

In an embodiment, the purse suturing device is used to perform a surgical procedure in which the tubular stapler head is introduced through the lumen of the hollow viscus until it is placed in a convenient position, including the anvil with the pole. The anvil is in the pursing position (i.e., the anvil is spaced apart from the staple carrier of the stapler head). The thread is then placed around the viscus in the region between the anvil and the staple carrier. The thread is wound and tightened against the pole of the anvil to create a tightened region of the wall of the viscus. In the tightened region, a fold in the hollow viscus is formed between the staple carrier and the anvil. The fold includes a first layer of the viscus and a second layer of the viscus proximate to and folded against the first layer of the viscus.

The pole of the anvil is now displaced concentrically along the interior of the stapler head to the "closed" or stapling position, in which the pursed wall of the hollow viscus is compressed. The first and second layers of the viscus in the pursed region are folded between the anvil and the staple carrier. The suturing device is now fired by means of the actuator of the handle, causing the tubular stapler head to be displaced concentrically along the interior of the tubular case. The tubular stapler head pushes staples carried by the staple carrier through the folded layers of the viscus, securing the folded layers together in a folded position. In this manner, a secured folding that contains the thread is formed.

In accordance with an embodiment, the hollow viscus is cut at the level of the anvil or the stapler head to obtain a purse suture at the end of said hollow viscus.

Thus, in accordance with an embodiment, a purse-suturing device for suturing a hollow viscus includes a circular stapler which includes a tubular case configured to be inserted inside a portion of a hollow viscus, a tubular stapler head disposed in a first interior of the tubular case and configured to be displaced concentrically along the interior of the tubular case and to push staples, a staple carrier, and a handle comprising an actuator connected to the tubular stapler head. The device also includes an anvil against which staples are folded, the anvil having a pole configured to be displaced concentrically along a second interior of the tubular stapler head, and a suturing thread configured to be wound around the hollow viscus and tightened around a selected section of a wall of the hollow viscus. The pole of the anvil is configured to be displaced between a pursing position in which the anvil is retracted a selected distance from the stapler head, defining a space between the anvil and the stapler head and an associated section of the wall of the hollow viscus around which the suturing thread is wound, and a stapling position in which the anvil is proximate the stapler head, compressing and folding the section of the wall of the hollow viscus.

In one embodiment, the anvil comprises a plurality of grooves adapted to provide a surface against which the staples are folded.

In another embodiment, the staple carrier comprises a plurality of projections adapted to hold the staples.

In another embodiment, the suturing thread comprises a plastic monofilament.

In another embodiment, the suturing thread comprises a polypropylene.

In another embodiment, the device also includes a pushing stick configured to receive first and second ends of the suturing thread and to fasten the suturing thread around the hollow viscus and the pole.

In another embodiment, the circular stapler is attachable to a conventional circular stapler.

The features, functions and advantages that have been discussed can be achieved independently in various embodiments or may be combined in yet other embodiments. Further details of which can be seen with reference to the following description and drawings.

BRIEF DESCRIPTION OF THE DRAWINGS

FIG. 5a shows a cross-sectional view of the device and the thread of FIG. 4a.

FIG. 6b shows a perspective view of the suturing device of FIG. 6a.

FIG. 8b shows a perspective view of the suturing device and the pushing stick of FIG. 8a.

FIG. 13b shows a perspective view of the suturing device and hollow viscus of FIG. 13a.

FIG. 17b shows a perspective view of FIG. 17a.

FIG. 19b shows a perspective view of FIG. 19a.

FIG. 21b shows a perspective view of the hollow viscus of FIG. 21a.

DETAILED DESCRIPTION

Figure 1A:
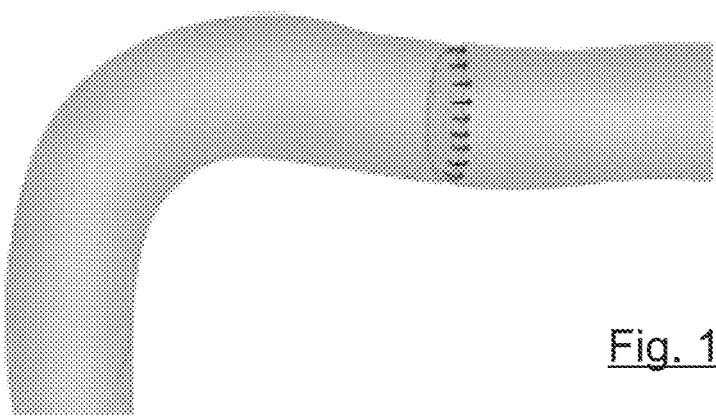
FIG. 1a shows an end-to-end anastomosis.
Figure 1B:
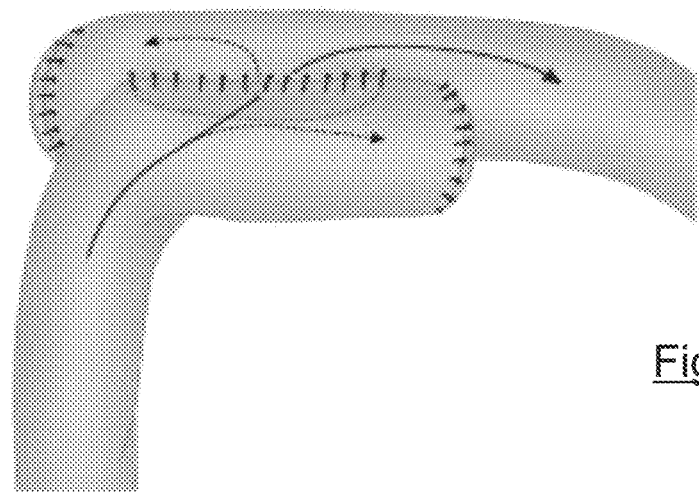
FIG. 1b shows a side-to-side anastomosis.
Figure 1C:
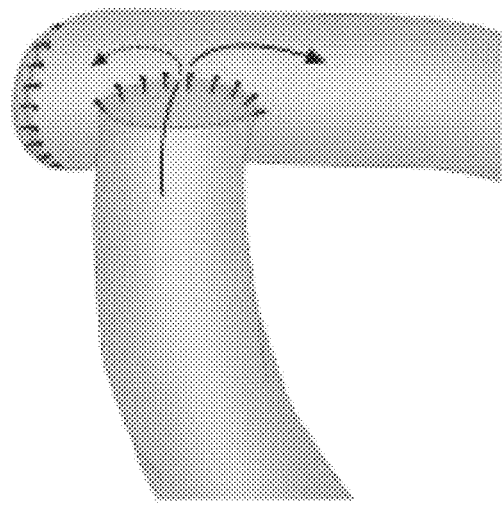
FIG. 1c shows an end-to-side anastomosis.
Figure 2:
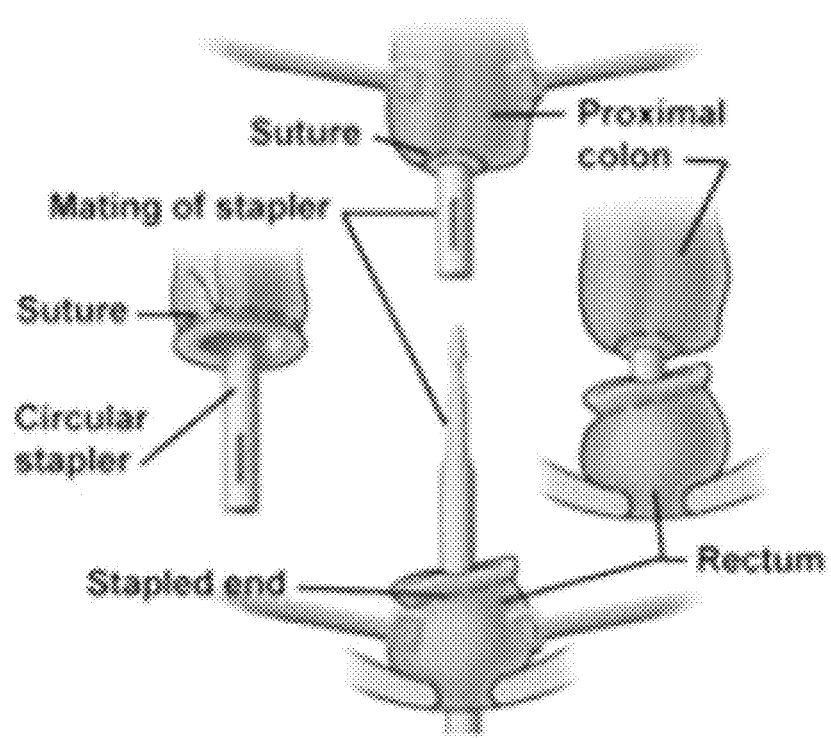
FIG. 2 shows a mechanical low rectal anastomosis being performed using a circular stapler.
Figure 3:
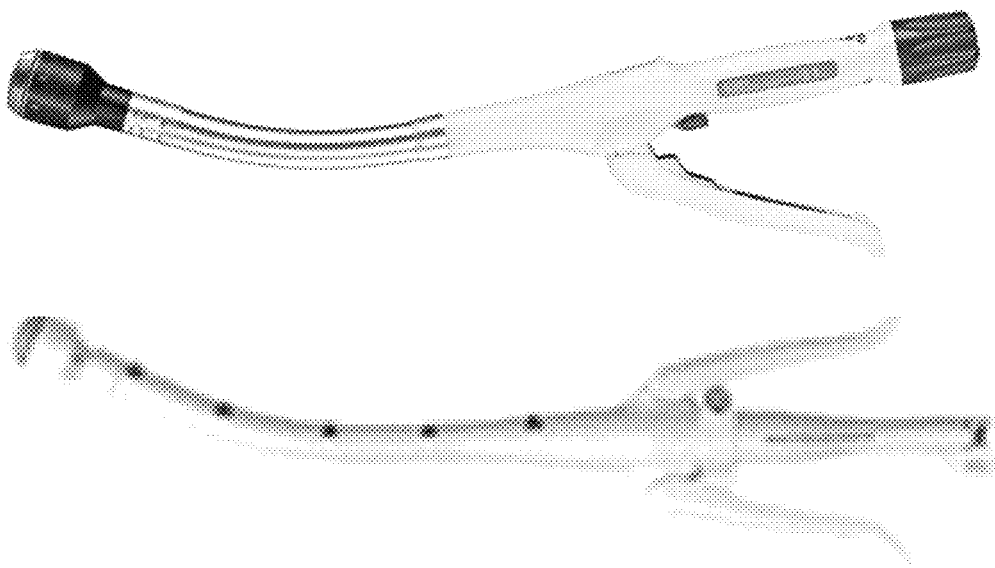
FIG. 3 shows two conventional circular staplers that may be used for esophageal and rectal anastomosis.
Figure 4A:
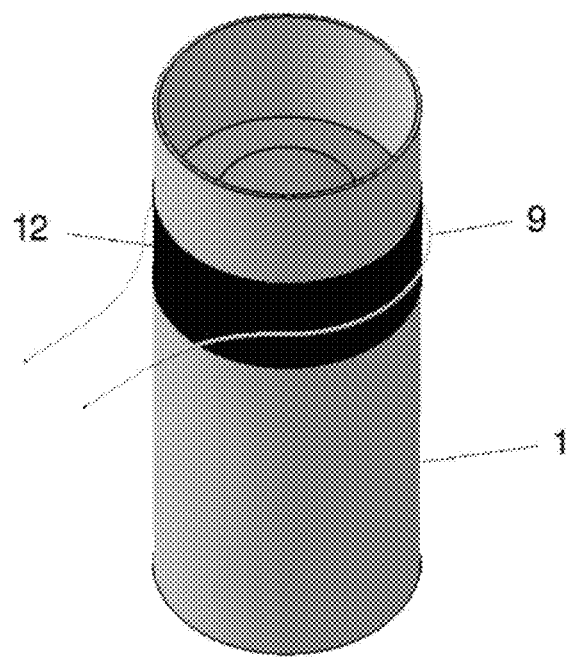
FIG. 4a shows a perspective view of a suturing device inserted in a section of a hollow viscus, in a pursing position, and a thread surrounding the hollow viscus, in accordance with an embodiment.
Figure 4B:
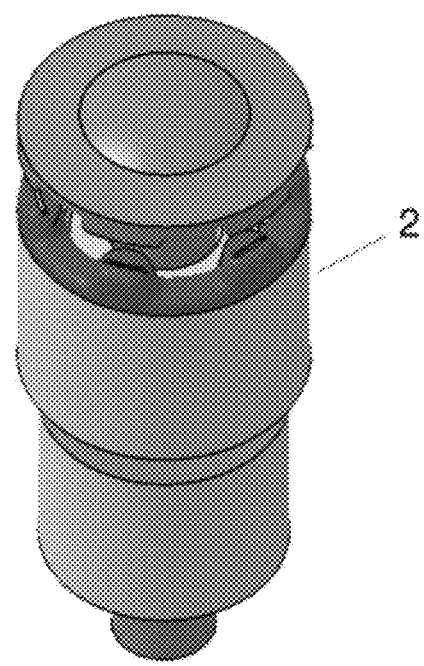
FIG. 4b shows the device itself according to an embodiment but without the thread.
Figure 4C:
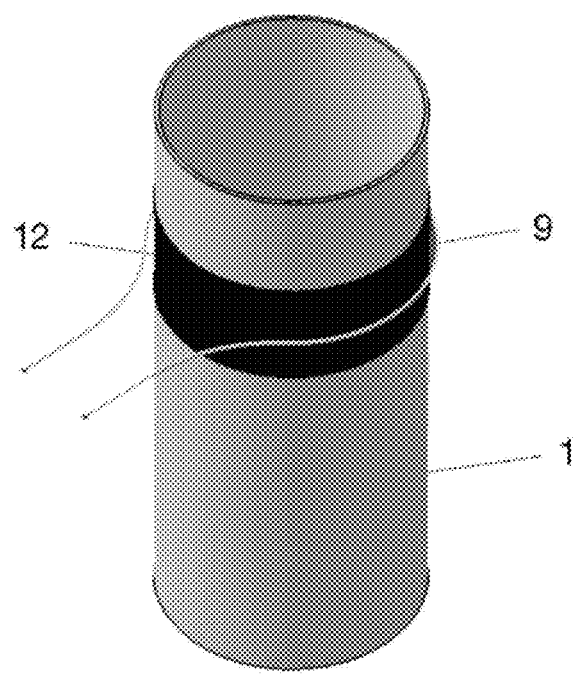
FIG. 4c shows the hollow viscus along with the thread to be used with the device.
Figure 4D:
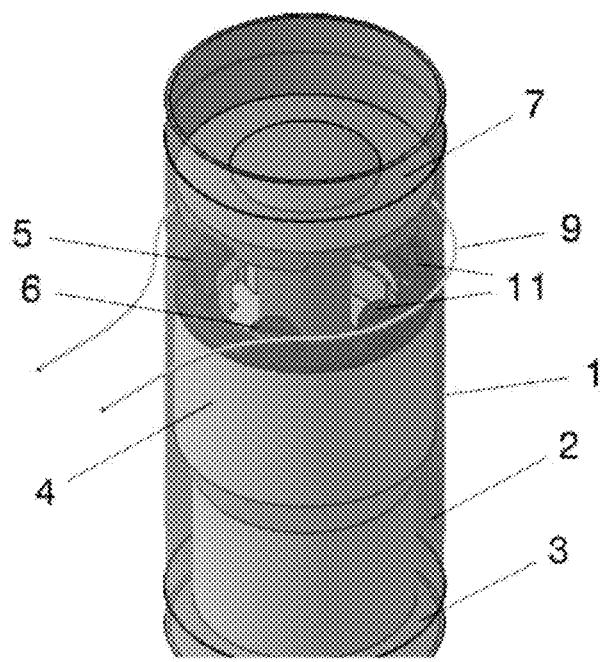
FIG. 4d shows the hollow viscus with the device inserted and the thread in place, said hollow viscus represented transparent to show the different parts of the inserted device.
Figure 5A:
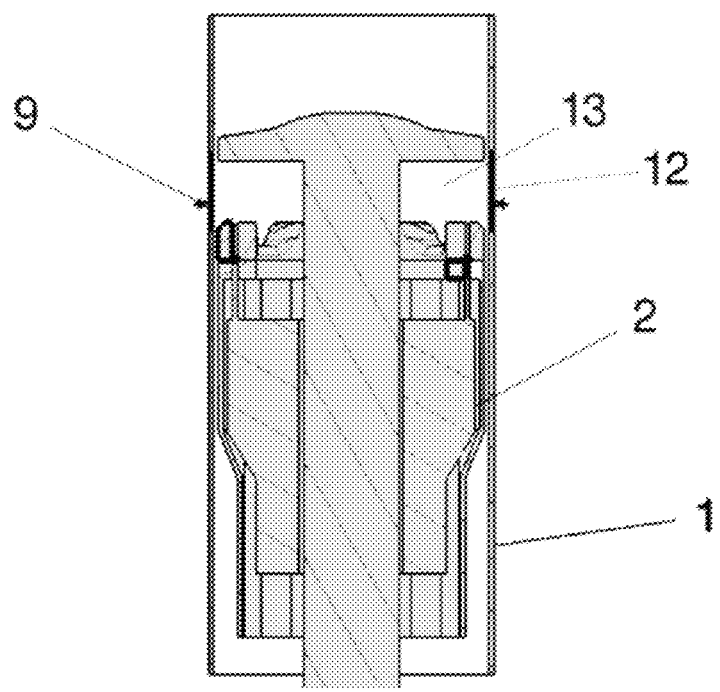
Figure 5B:
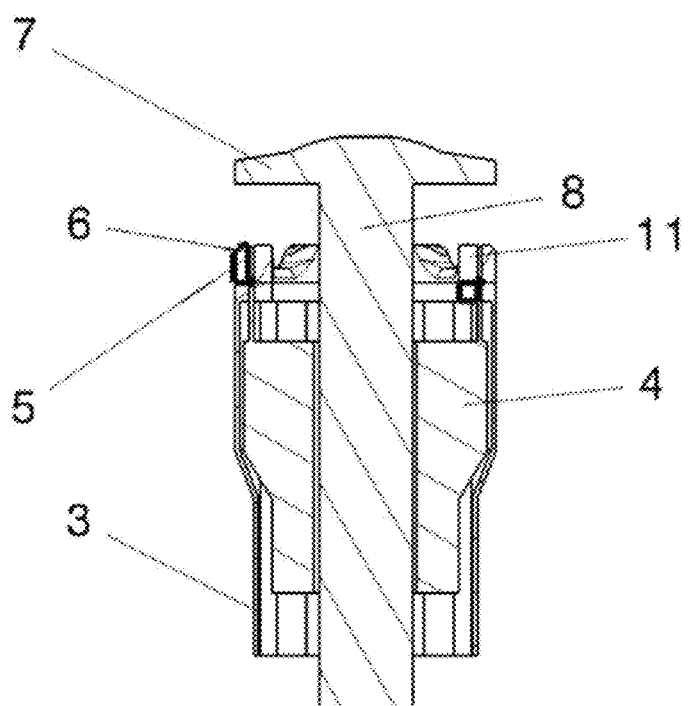
FIG. 5b shows a cross-sectional view of FIG. 4b.
Figure 5C:
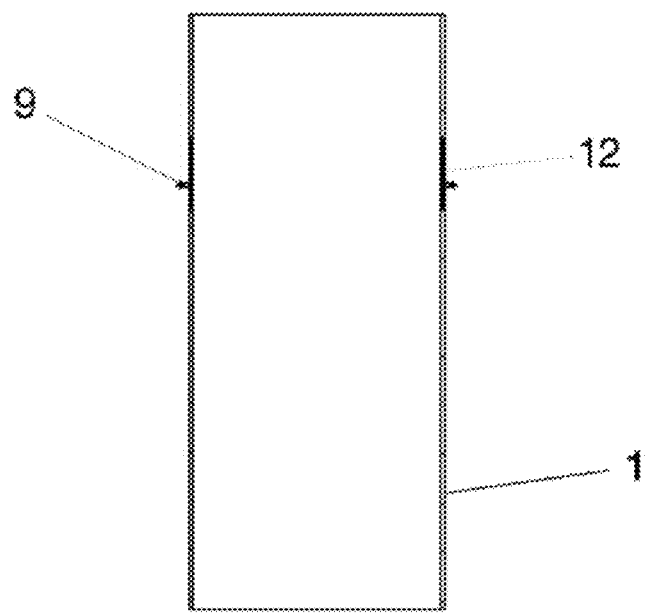
FIG. 5c shows a cross-sectional view of FIG. 4c.
Figure 5D:
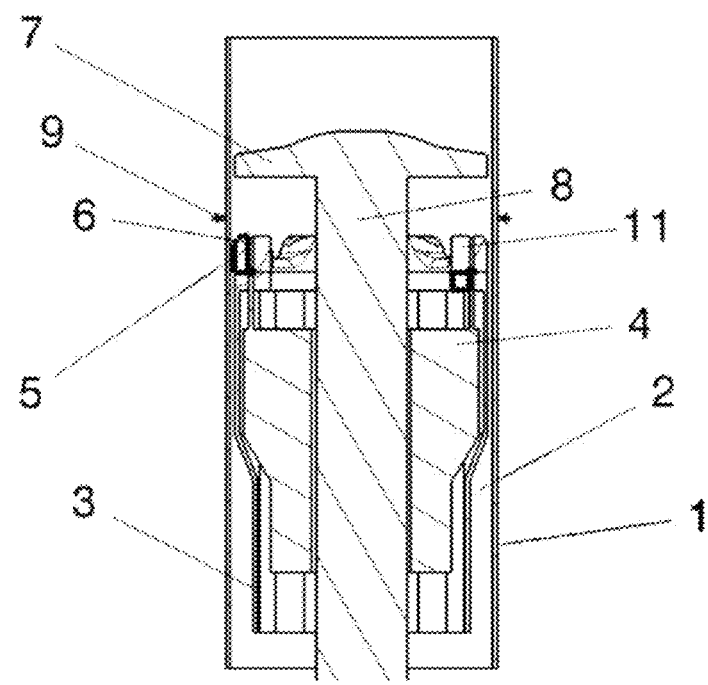
FIG. 5d shows a cross-sectional view of FIG. 4d.

In accordance with an embodiment, a purse suturing device for suturing a hollow viscus is provided. In one embodiment, the device includes a circular stapler and a suturing thread.

In accordance with another embodiment, a purse-suturing device for suturing a hollow viscus includes a circular stapler which includes a tubular case configured to be inserted inside a portion of a hollow viscus, a tubular stapler head disposed in a first interior of the tubular case and configured to be displaced concentrically along the interior of the tubular case and to push staples, a staple carrier, and a handle comprising an actuator connected to the tubular stapler head. The device also includes an anvil against which staples are folded, the anvil having a pole configured to be displaced concentrically along a second interior of the tubular stapler head, and a suturing thread configured to be wound around the hollow viscus and tightened around a selected section of a wall of the hollow viscus. The pole of the anvil is configured to be displaced between a pursing position in which the anvil is retracted a selected distance from the stapler head, defining a space between the anvil and the stapler head and an associated section of the wall of the hollow viscus around which the suturing thread is wound, and a stapling position in which the anvil is proximate the stapler head, compressing and folding the section of the wall of the hollow viscus.

In accordance with an embodiment, the device may be used to perform a purse suture at a hollow viscus. For example, the device may be used to prepare a mechanic end-to-end anastomosis or a side-to-end circular anastomosis.

In accordance with an embodiment, the purse suturing device includes a circular stapler and a suturing thread. The circular stapler has a tubular stapler head adapted to be inserted inside a section of the hollow viscus to be sutured, a handle with an actuator connected to the stapler head, and an anvil against which the staples may be folded. The anvil has a pole adapted to be inserted into the tubular stapler head. In one embodiment, the suturing thread is wound around the hollow viscus and tightened, causing a section of the hollow viscus to be tightened around the pole. The tightened section of the hollow viscus has a reduced radius. The tightened section also includes a pursed, or folded, section of the wall of the hollow viscus, in which two layers of the wall of the hollow viscus are prepared to be stapled together.

FIGS. 4a-4d show a perspective view of a purse-suturing device inserted in a section of a hollow viscus and a thread surrounding the hollow viscus, in accordance with an embodiment. FIGS. 5a-5d show a cross-sectional view of the device and the thread of FIGS. 4a-4d.

The purse-suturing device includes a circular stapler 2 and a suturing thread 9. The circular stapler 2 has a tubular case 3 configured to be inserted inside a section of a hollow viscus 1. The circular stapler 2 also includes a tubular stapler head 4 disposed in the interior of the tubular case 3 and configured to be displaced concentrically along the interior of the tubular case 3. The purse-suturing device also includes an anvil 7, which has a pole 8 configured to be displaced concentrically along the interior of the stapler head 4. The purse-suturing device also includes a staple carrier 5 that holds a plurality of staples 6. The stapler head 4 is adapted to push staples 6, located in a staple carrier 5, against anvil 7 in order to cause the staples to fold into a folded position. The purse-suturing device also includes a handle with an actuator connected to the stapler head 4.

The pole 8 of the anvil 7 is configured to be displaced between a pursing position and a stapling position of the circular stapler 2.

FIGS. 4a-4d and 5a-5d show the purse-suturing device in the pursing position. In particular, when in the pursing position, the anvil 7 is retracted from the stapler head 4, creating a space between the anvil 7 and the stapler head 4. The space between the anvil 7 and the staple carrier 5 creates a pursing region 12 of the hollow viscus 1, which is a region of the hollow viscus 1 that may be tightened against the pole 8 of the anvil 7, and then folded and stapled.

In accordance with an embodiment, the suturing thread 9 is configured to be wound around the hollow viscus 1. The thread 9 has a loose position and a tightened position. In FIGS. 4a-4d and 5a-5d, the thread 9 is shown in the loose position.

In accordance with an embodiment, when the anvil 7 is in the pursing position, the thread 9 may be tightened, causing a portion of the wall of the hollow viscus 1 in the pursing region 12 to be tightened against the pole 8 of the anvil 7, thereby pursing the wall of the hollow viscus 1.

Figure 6A:
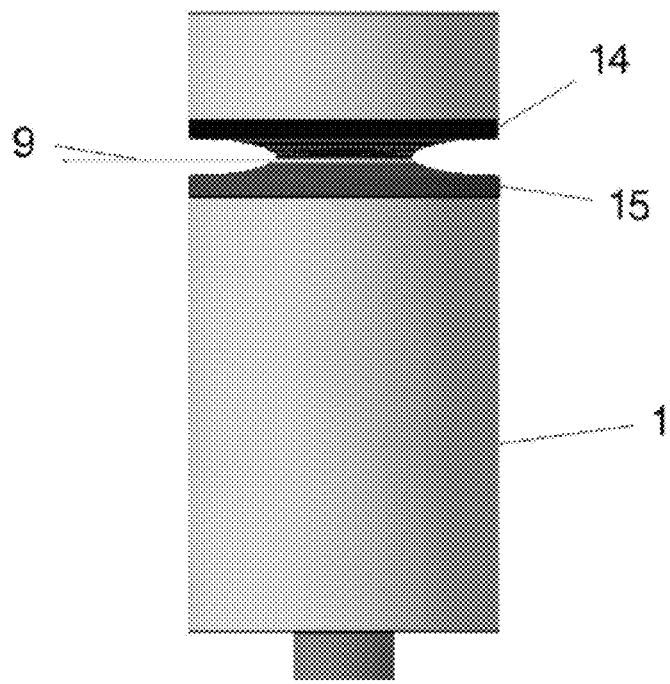
FIG. 6a shows the suturing device of FIGS. 4a-5a in a pursing position, and the thread in a tightened position, in accordance with an embodiment.
Figure 6B:
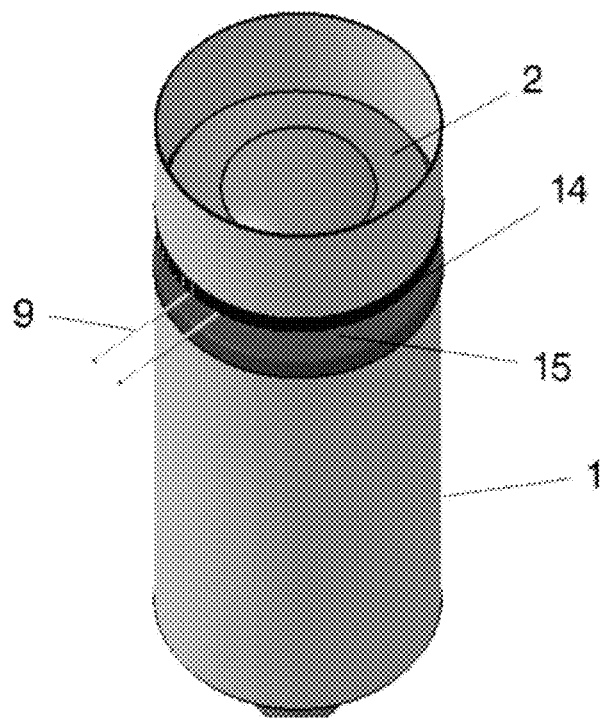
Figure 6C:
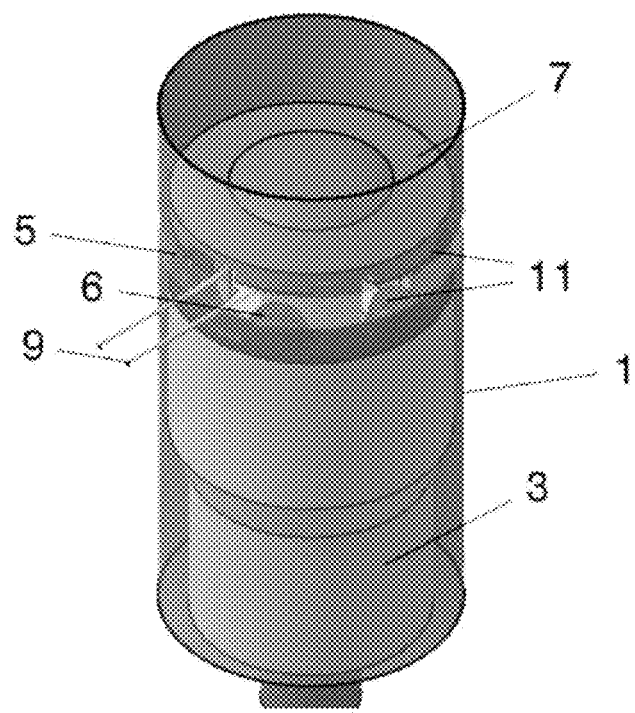
FIG. 6c shows the hollow viscus of FIGS. 6a-6b transparent to show the different parts of the inserted device.
Figure 7:
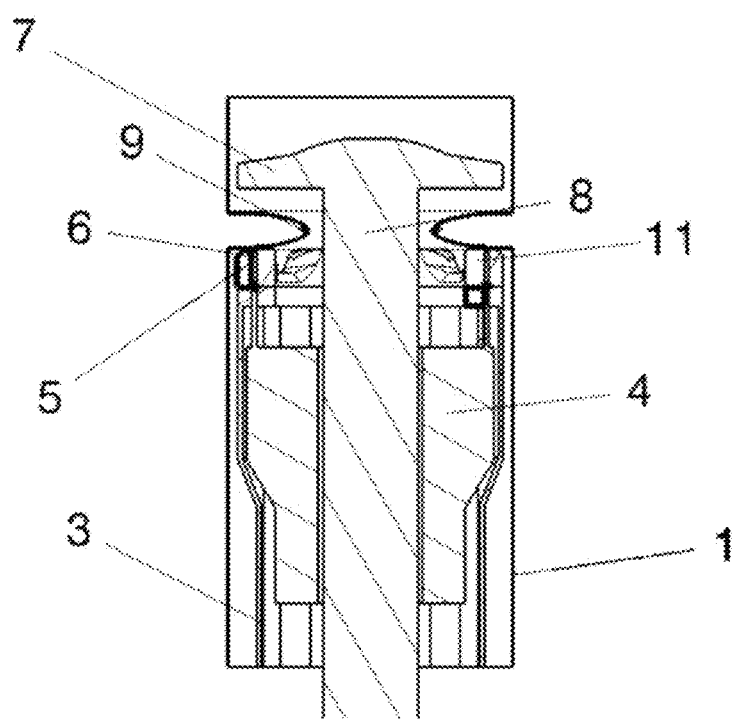
FIG. 7 shows a cross-sectional view of the device of FIGS. 6a-6c in a pursing position.

FIGS. 6a-6c shows the suturing device in the pursing position, and the thread 9 in the tightened position, in accordance with an embodiment. FIG. 7 shows a cross-sectional view of the device in the pursing position of FIG. 6a-6c.

As shown in FIGS. 6a-6c and 7, when the suturing device is in the pursing position and the thread 9 is in the tightened position, the wall of the hollow viscus 1 in the pursing region 12 of FIGS. 4a-4d and 5a-5d is folded and ready to be stapled. Specifically, a first section 14 of the wall of the hollow viscus 1 is proximate and ready to be stapled to a second section 15 of the wall of the hollow viscus 1.

Thus, in accordance with an embodiment, the purse-suturing device is used in a surgical method in which the tubular stapler head 4 is introduced through the lumen of the hollow viscus 1 until it is placed in a convenient position, in which the anvil 7 is spaced apart from the staple carrier 5, in the pursing position, as shown in FIGS. 4a-7. The pursing thread 9 is placed around the viscus 1 and tightened against the pole 8 of the anvil 7 in order to create a fold in the pursing region 12 of the wall of the hollow viscus 1 between the staple carrier 5 and the anvil 7.

In one embodiment, the suturing thread 9 may be knotted around the pole 8 of the anvil 7 in order to maintain the pursing thread 9 tighten.

As explained above, the function of this purse-suturing device is mainly preparing one end of the hollow viscus to be sutured to another end by means of a circular stapler, creating a purse suture in certain locations where it is almost impossible or extremely difficult to create a hand-sewn purse suture. However, this device does not make the anastomosis, so this purse-suturing device must allow the introduction of a circular stapler to make the anastomosis after the purse suture. Two alternatives are possible: either the purse-suturing device is attached to a circular stapler or the purse-suturing device must be removed to allow the introduction of an independent circular stapler.

If both suturing heads are placed together in a single device (obviously with one handle and two actuators), then the pursing thread 9 can be wound around the hollow viscus 1 and the pole 8 of the anvil 7 and tightened with a knot (that prevents loosening) before the purse suture device is activated. Once the purse-suture is made, it is secured around the pole 8 of the anvil 7 and it is only the anvil 7 which has to be detached and interchanged with a new anvil (along with the other end of the hollow viscus 1) to create the circular anastomosis.

Alternatively, if both, the purse-suture and circular suturing devices are to be used independently, the pursing thread 9 cannot be tight knotted around the hollow viscus 1, to let the purse suture to be open to allow the removal of the purse suturing device and the introduction of the circular suturing device. However, while the purse-suturing device is in the suturing position, the pursing thread 9 has to be tighten (but not knotted) around the hollow viscus 1, to create the proper folding in said hollow viscus 1 and to fasten the thread 1 into the pursing region 12. This tightening of the thread 9 is obtained by means of a pushing stick 10. Said pushing stick 10 has one or two holes in the tip thereof through which the ends of the pursing thread 9 are to be threaded surrounding the hollow viscus 1. Once the purse suturing device is placed in the proper location, in the pursing position, the thread 9 is fastened by pushing with the pushing stick 10 to create the folding of the hollow viscus 1 around the pole 8. Afterwards, the device is turned into the suturing position while the pushing stick 10 fastens the thread 9. Projections 11 and recesses of the stapler carrier 4 allow the pushing stick 10 to push against the pole 8 while the device is in the suturing position. These projections 11 and recesses may be combined with bevel inclined slots 17 and anvil projections 18 in the anvil 17, which provide space to push and fasten the thread 9 with the pushing stick 10. Once the staples are folded the stick can be removed allowing the pursing to be opened when necessary.

Figure 8A:
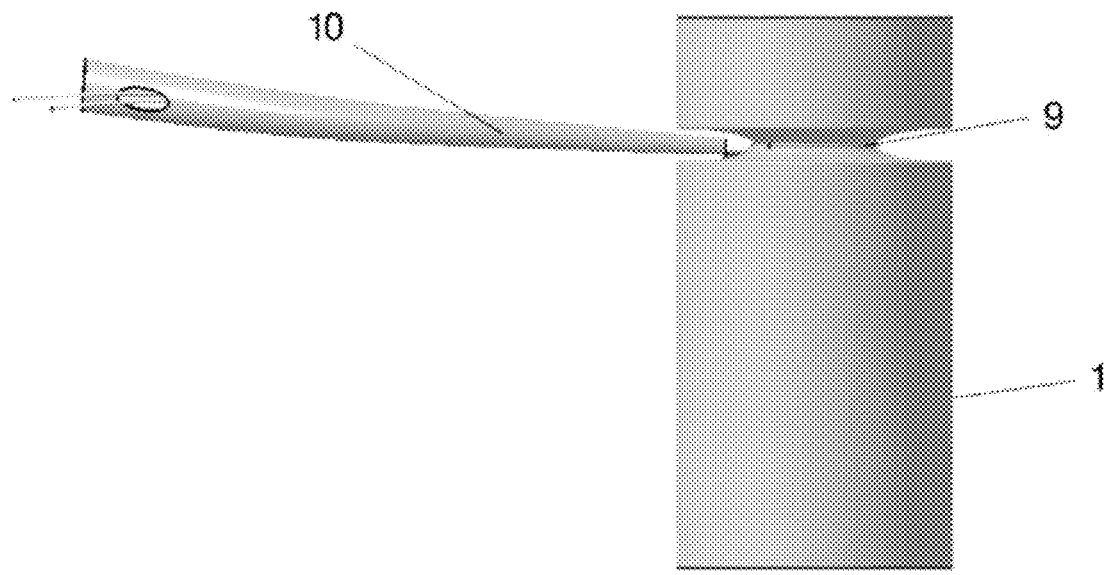
FIG. 8a shows a suturing device in a pursing position, and a pushing stick used for fastening the thread, in accordance with an embodiment.
Figure 8B:
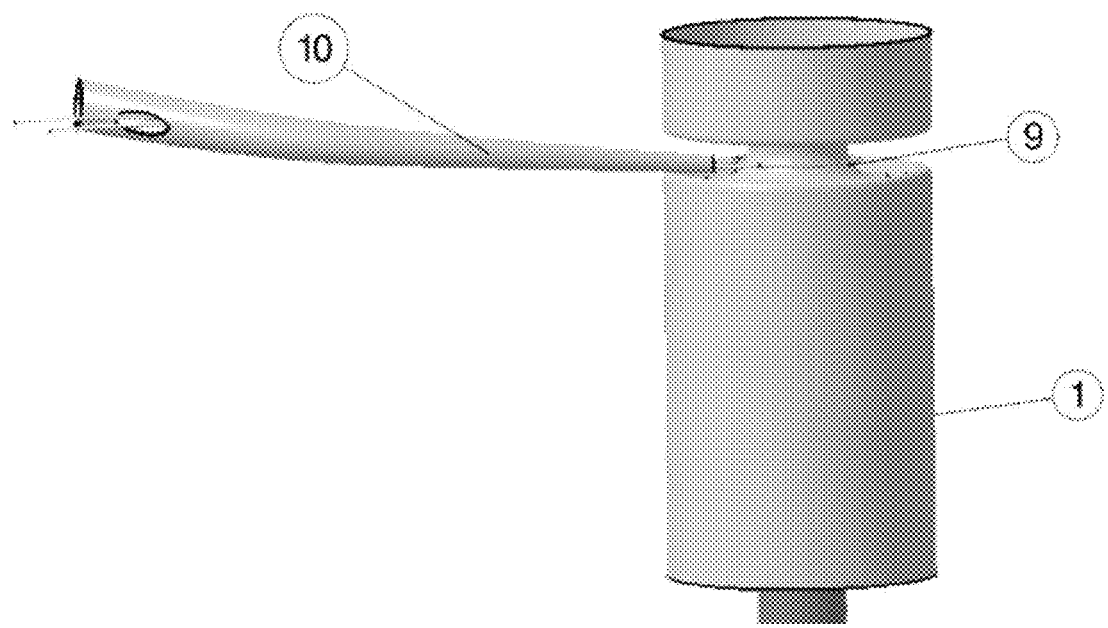
Figure 8C:
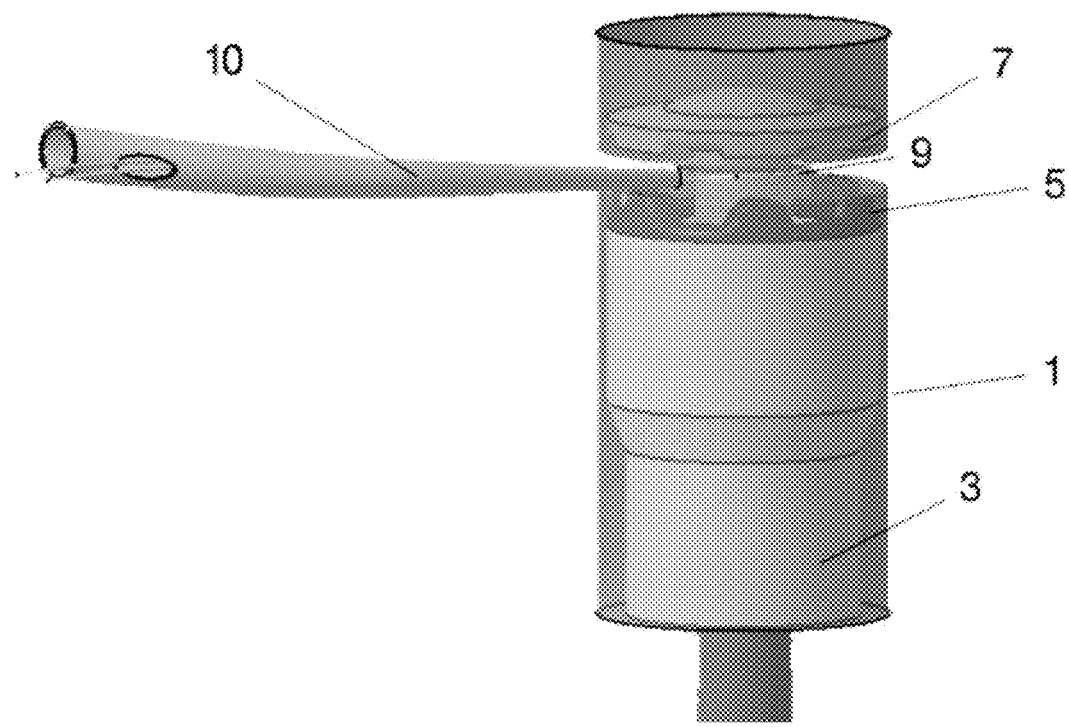
FIG. 8c shows a perspective transparent view such that the stick is inserted taking advantage of the space in between projections.
Figure 9:
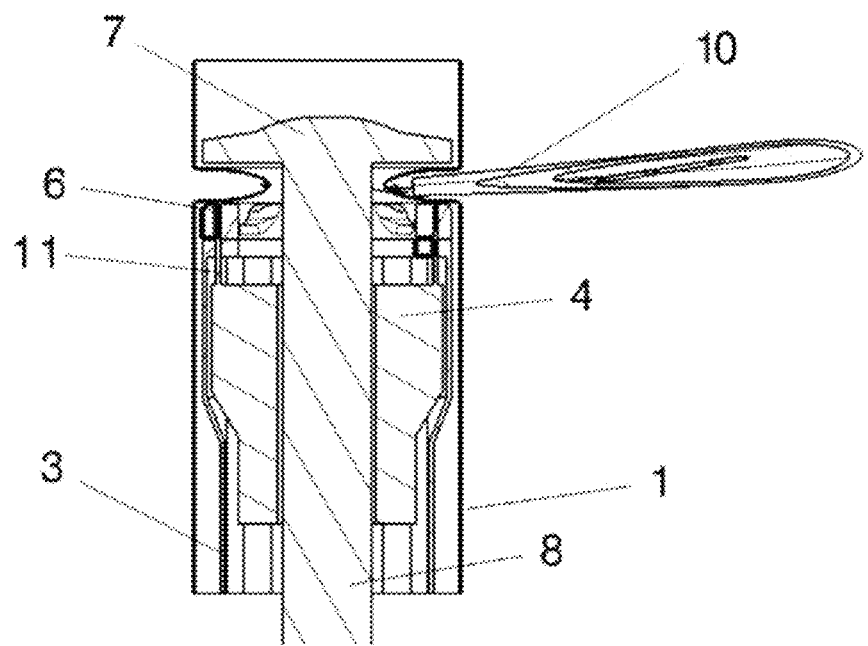
FIG. 9 shows a cross-sectional view of the suturing device and the stick of FIGS. 8a-8c.

FIGS. 8a-9 show the suturing device and a pushing stick in accordance with an embodiment. More particularly, FIGS. 8a-9 illustrate the use of the stick 10 to fasten the suturing thread 9 around the pole 8 inside the hollow viscus 1.

Figure 10:
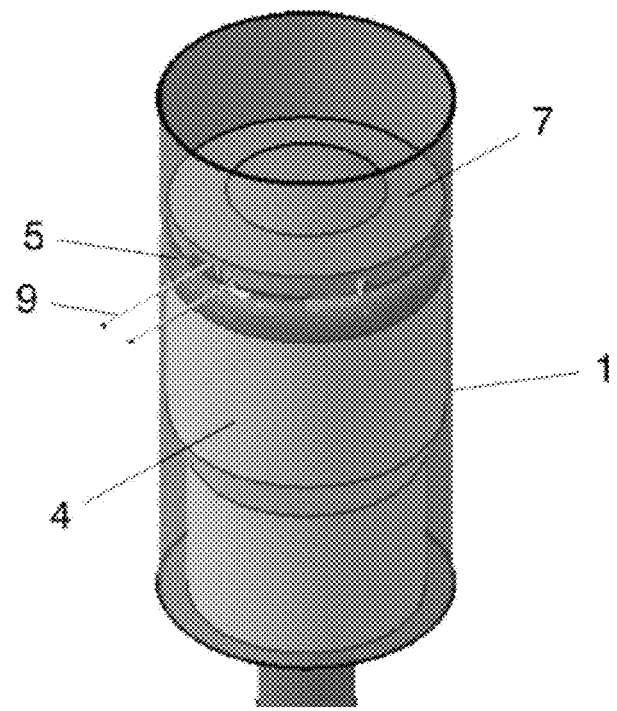
FIG. 10 shows a suturing device in a stapling position, in accordance with an embodiment.
Figure 11:
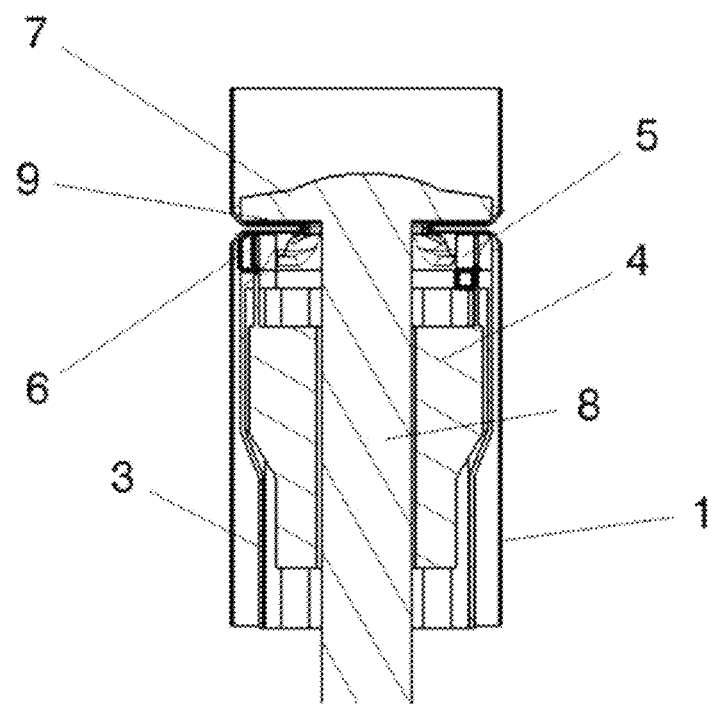
FIG. 11 shows a cross-sectional view of the suturing device of FIG. 10.

After the thread 9 has been tightened, the pole 8 of the anvil 7 is displaced concentrically along the interior of the stapler head 4 to the stapling position, where the pursing region 12 of the wall of the hollow viscus 1 is compressed and folded between the anvil 7 and the staple carrier 5. FIGS. 10-11 show the suturing device in the stapling position in accordance with an embodiment. The wall of the viscus 1 is folded and fixed by the suturing thread 9 in the space existing between the staple carrier 5 and the anvil 7.

FIGS. 10 and 11 show the purse-suturing device in the stapling position in accordance with an embodiment. In the stapling position, the anvil 7 is proximate the staple carrier 5, in a position such that the pursing region 12 of the wall of the hollow viscus 1 is compressed and folded between the anvil 7 and the staple carrier 5. Specifically, the first section 14 of the wall of the hollow viscus 1 is folded against the second section 15 of the wall of the hollow viscus 1.

The suturing thread 9 may be made from different materials and have different sizes. In one embodiment, the thread comprises a plastic monofilament such as polypropylene.

In accordance with an embodiment, the anvil 7 has a plurality of grooves 16 that provide a surface against which staples 6 are folded.

Referring to FIGS. 4a-7, the staple carrier 5 of the stapler head 4 may comprise a plurality of projections 11 which hold the staples 6. The projections 11 are separated from each other by a selected distance in order to ensure that the pushing stick 10 can easily cross the stapling line to fasten the pursing thread 9 with the wall of the hollow viscus 1 around the pole 8 of the anvil 9.

In accordance with an embodiment, the circular stapler 2 of the purse-suturing device may be attached to a conventional circular stapler.

Figure 24:
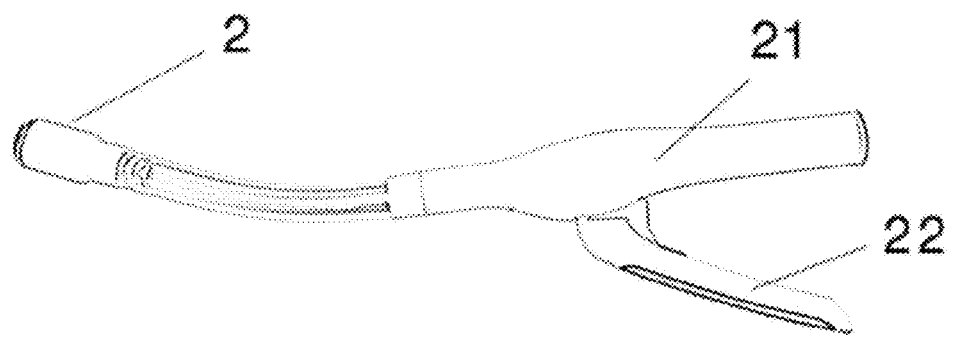
FIG. 24 shows the suturing device with a handle and an actuator in accordance to an embodiment.

FIG. 24 shows a suturing device in accordance with an embodiment. The suturing device includes a handle 19 that includes an actuator 20. The suturing device also includes circular stapler 2 (with staple carrier 5), suturing thread 9 and anvil 7 (with pole 8).

Figure 12:
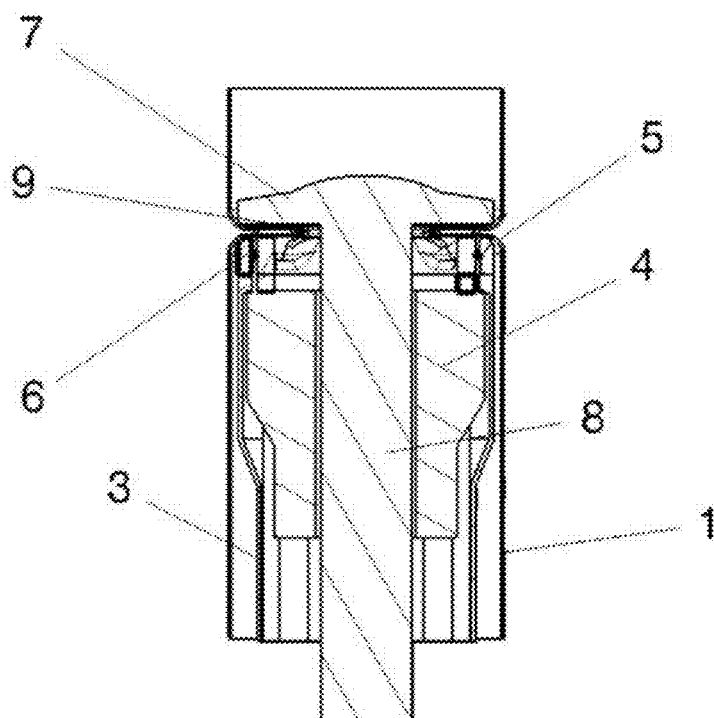
FIG. 12 shows a cross-sectional view of the suturing device of FIGS. 4a-7 in which staples ensure a folding of the walls of the viscus around the thread, in accordance with an embodiment.

In accordance with an embodiment, the suturing device is controlled by means of the actuator 20 of the handle 19, causing the tubular stapler head 4 to be displaced concentrically along the interior of the tubular case 3. The displaced tubular stapler head 4 pushes the staples 6 disposed in the staple carrier 5 through the folded sections 14,15 of the walls of the hollows viscus 1, creating a secured fold that contains the suturing thread 9. FIG. 12 shows the suturing device in the stapling position, in which the stapler head 4 has been fired, thereby driving the staples 6 out of the staple carrier 5 through the two sections 14,15 of the hollow viscus 1 to be folded by the anvil 7.

Figure 13A:
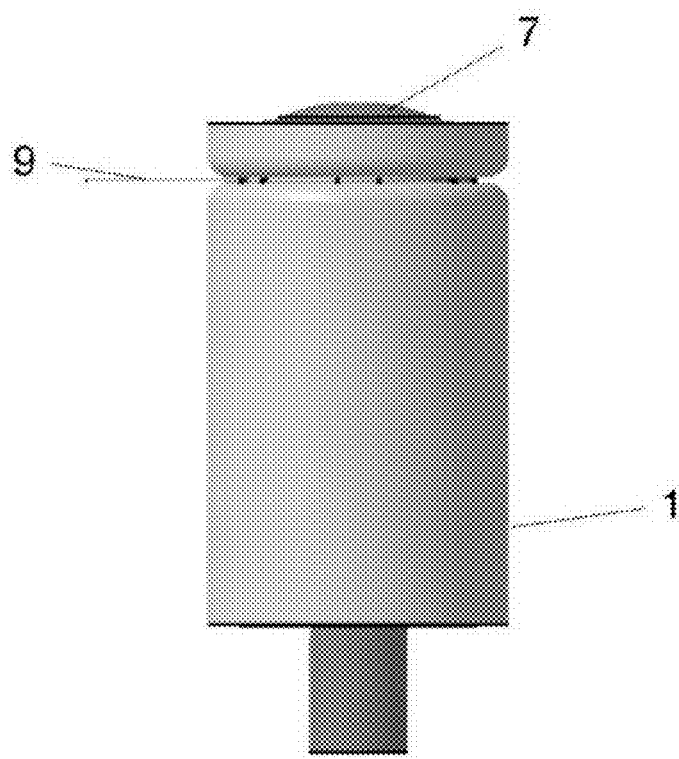
FIG. 13a shows a suturing device and a hollow viscus that has been cut over the anvil in accordance with an embodiment.
Figure 13B:
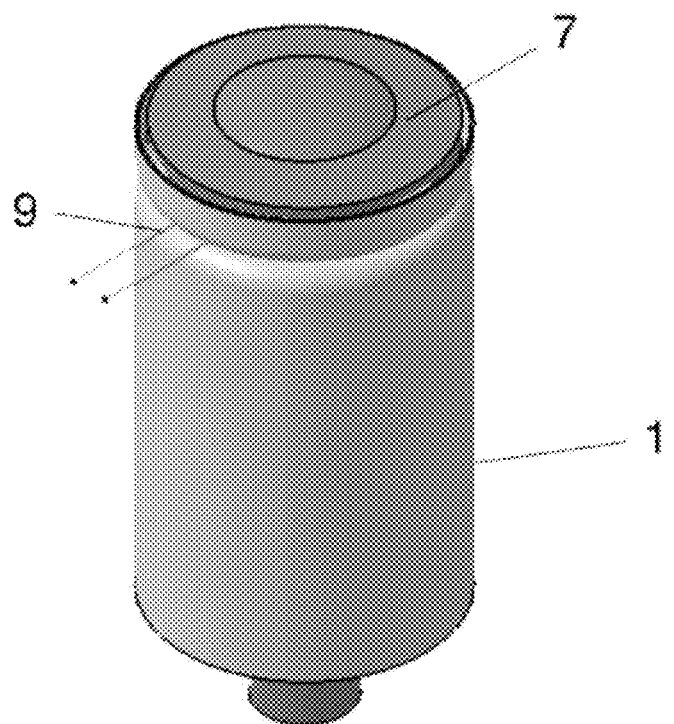
Figure 13C:
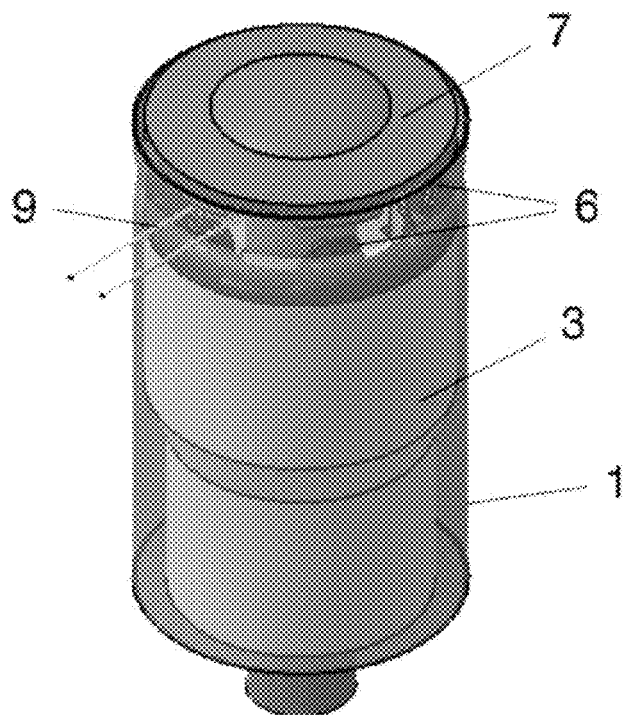
FIG. 13c shows a perspective view, the hollow viscus being transparent to show the inserted device.

In accordance with an embodiment, after the two sections 14,15 are stapled, the hollow viscus 1 is cut at the level of the anvil 7 or the stapler head 4 to form a hollow viscus 1 with a purse suture at the end thereof, as shown in FIGS. 13a-13c.

Figure 14:
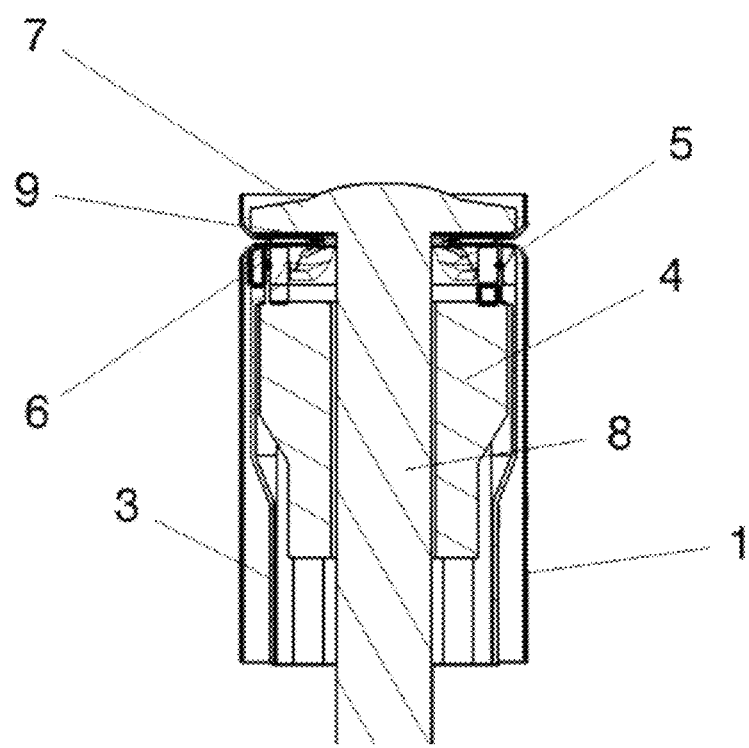
FIG. 14 is a cross-sectional view of the suturing device of FIGS. 13a-13c.
Figure 15A:
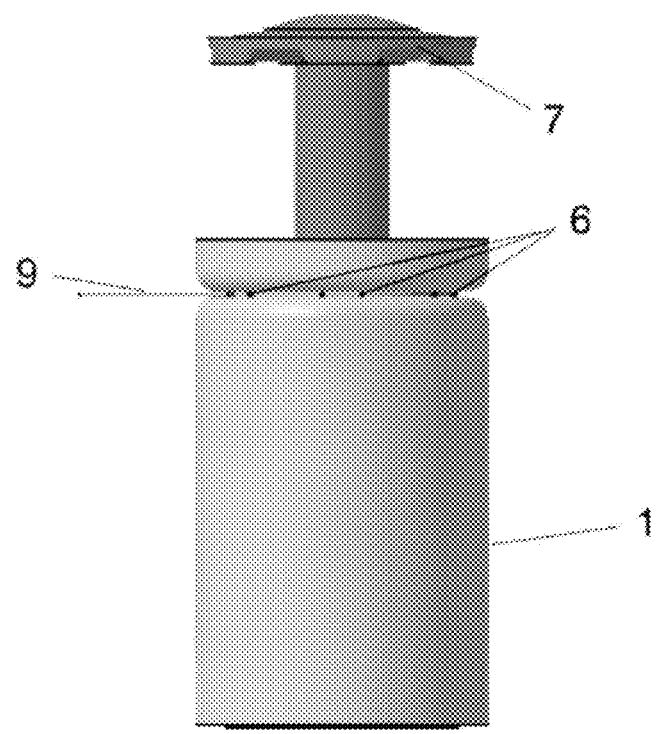
FIG. 15a shows a hollow viscus already cut and a suturing device in the pursing position in accordance with an embodiment. In this situation, the purse suture being released from being entrapped by the suturing device.
Figure 15B:
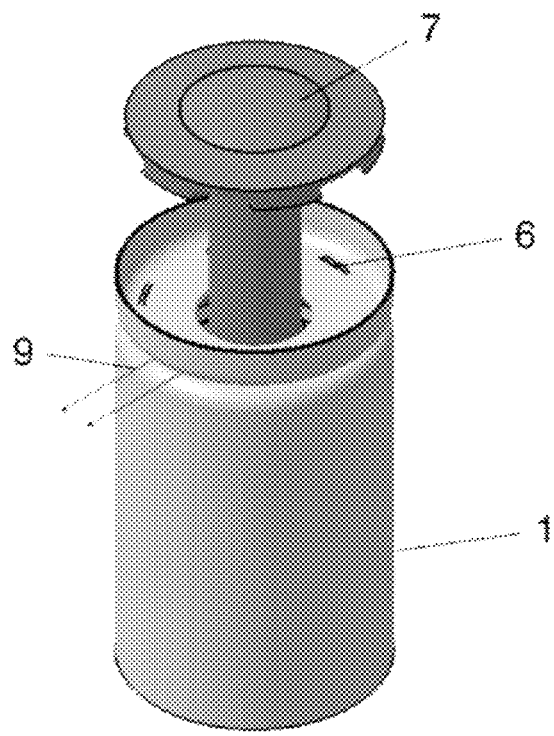
FIG. 15b shows a perspective view.
Figure 15C:
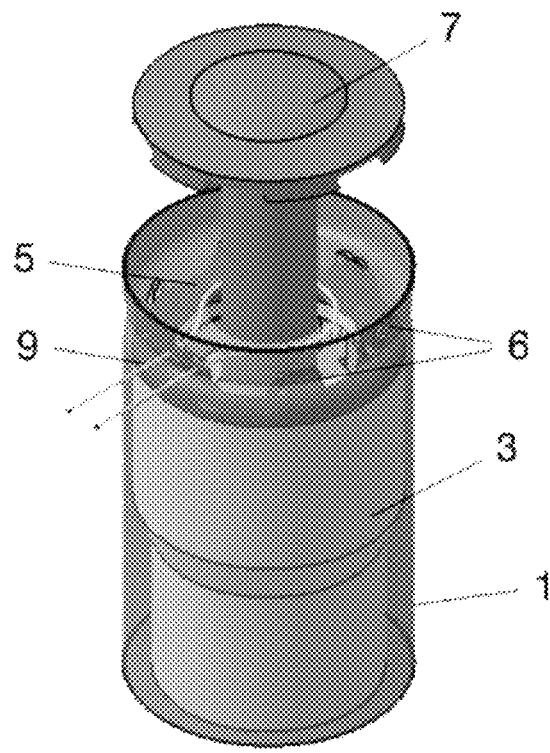
FIG. 15c shows the hollow viscus transparent to show the inserted device.
Figure 16:
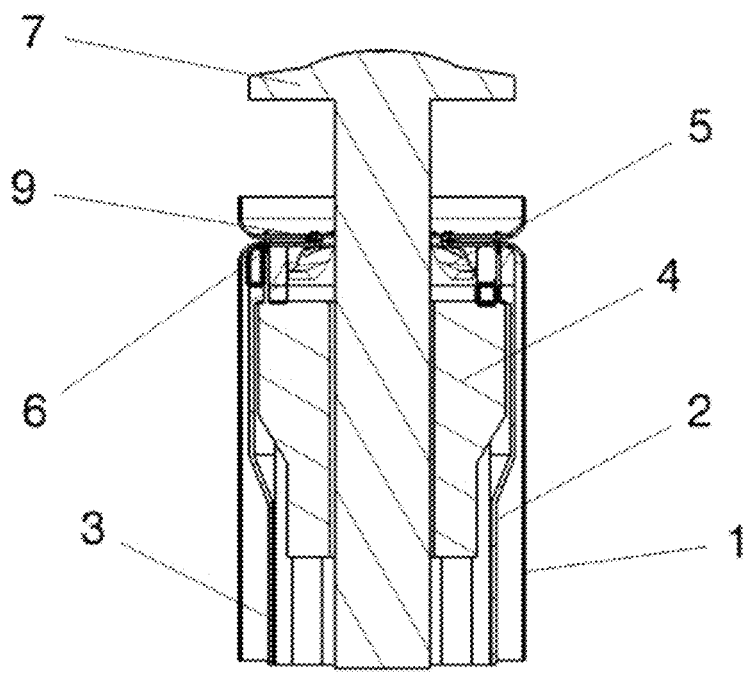
FIG. 16 is a cross-sectional view of the suturing device of FIGS. 15a-15c.

In accordance with an embodiment illustrated in FIGS. 14-15c, the pole 8 of the stapler head 4 is now retracted to the pursing position, releasing the pursing portion 12 of wall of the hollow viscus 1 from being compressed between the staple carrier 5 and the anvil 7.

Figure 17A:
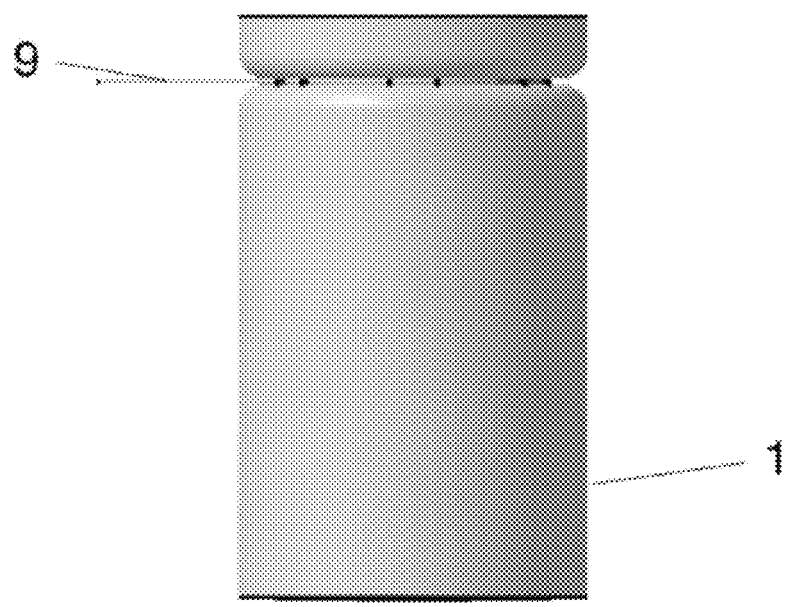
FIG. 17a shows a hollow viscus already cut and a suturing device with the anvil removed in accordance with an embodiment.
Figure 17B:
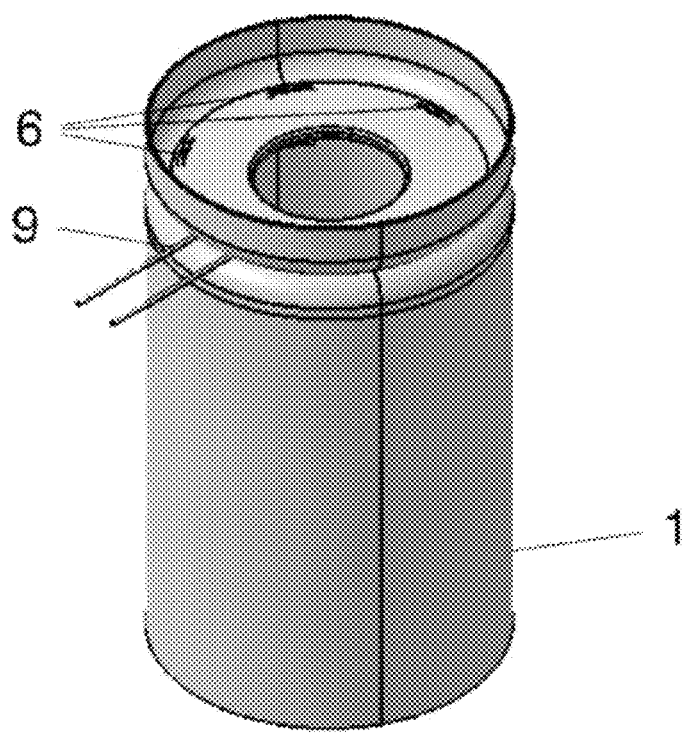
Figure 17C:
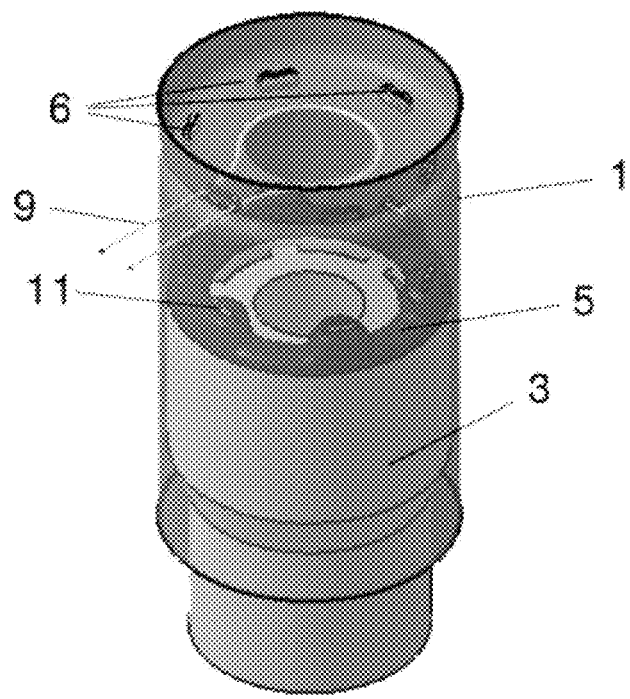
FIG. 17c shows the hollow viscus transparent to show the inserted device.
Figure 18:
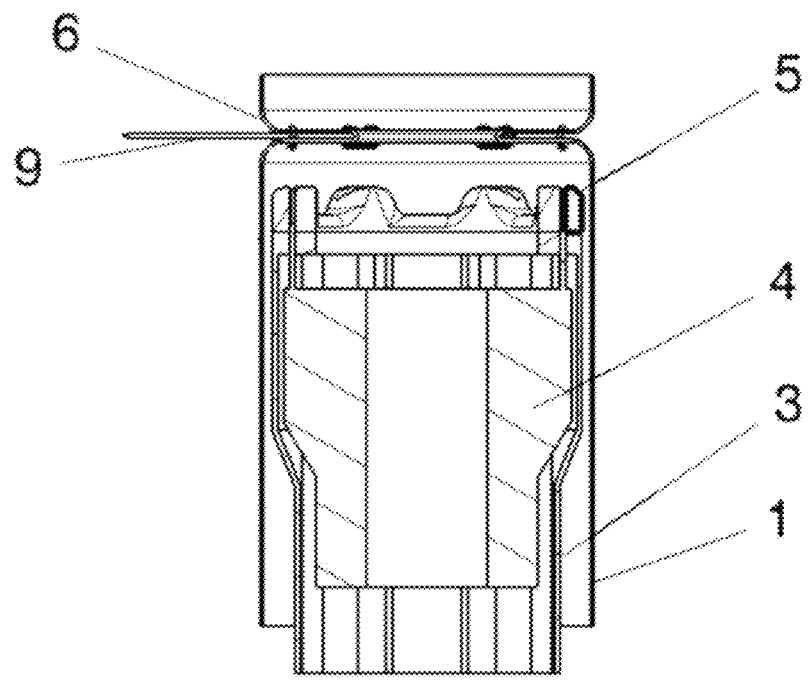
FIG. 18 is a cross-sectional view of the hollow viscus and suturing device of FIGS. 17a-17c.

From this moment on, two possible ways are considered according to how the suturing thread 9 was tightened, as explained above:

In accordance with an embodiment, a first method is used to remove the device from the hollow viscus 1 if the suturing thread was knotted around the hollow viscus 1 and pole 8. Specifically, the folded sections 14,15 remain knotted and secured in place by staples 6. FIGS. 15a-18 show a hollow viscus 1 in which the suturing thread 9 is knotted around the hollow viscus 1 and the pole 8 in accordance with an embodiment. The anvil 7 is now detached from the device and removed, as shown in FIGS. 17a-18. Afterwards, the tubular case 3 is removed from the hollow viscus 1, leaving the hollow viscus 1 with the thread 9 knotted and secured in place by the staples 6, as shown in FIGS. 17a-18.

In accordance with an embodiment, the stapler may be attached to a conventional circular stapler. The tubular case 3 is not removed after the removal of the anvil 7. Instead the tubular case 3 is kept in place until a new anvil is inserted with a second viscus ending to be anastomosed (connected) and a circular suture is performed to connect the second viscus to the hollow viscus 1. The blade of this conventional circular stapler breaks the pursing region 12 containing the staples 6 and the suturing thread 9 so that the staples 6 and suturing thread 9 may be removed after the anastomosis has been performed.

Figure 19A:
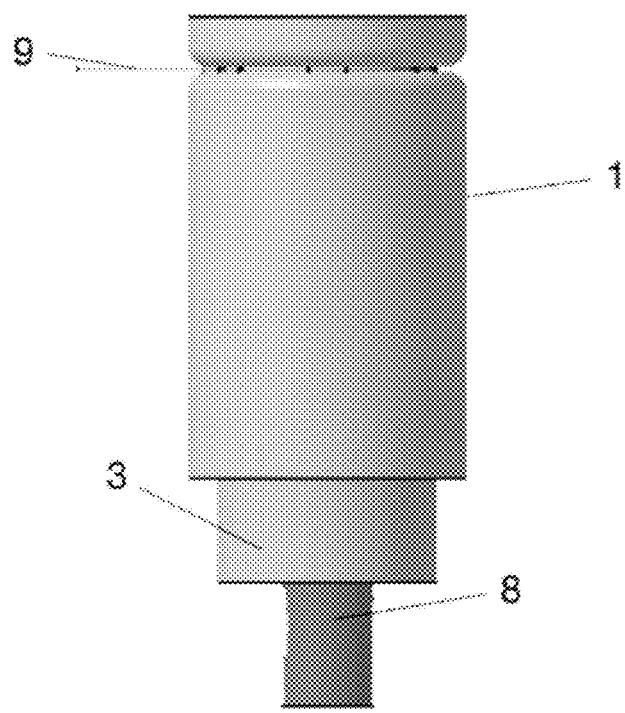
FIG. 19a shows a hollow viscus already cut and a suturing device with the anvil passed through the purse suture in accordance with an embodiment.
Figure 19B:
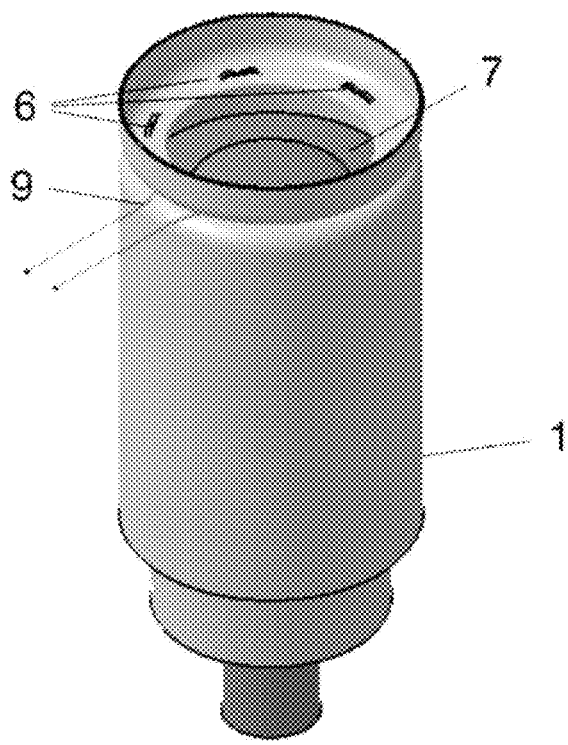
Figure 19C:
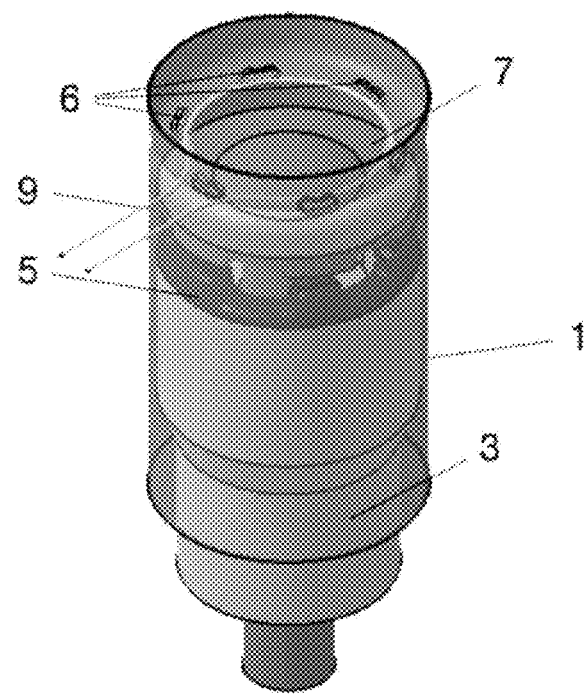
FIG. 19c shows the hollow viscus transparent to show the inserted device.
Figure 20:
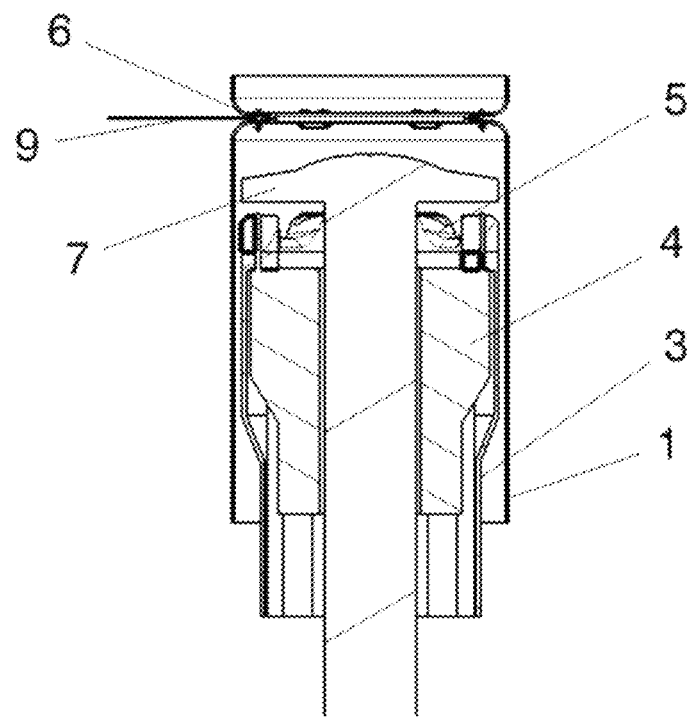
FIG. 20 is a cross-sectional view of the hollow viscus and stapler head of FIGS. 19a-19c.
Figure 21A:
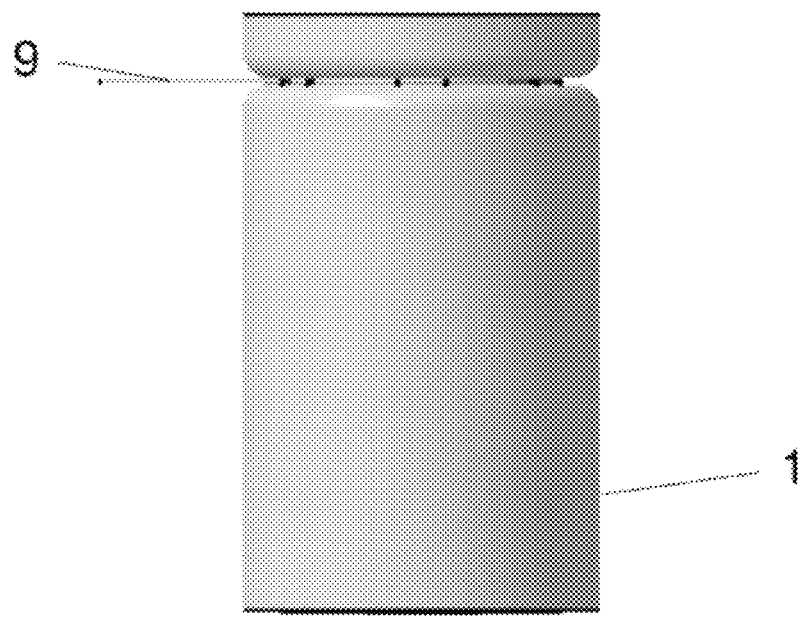
FIG. 21a shows a hollow viscus with a purse suture created and the suturing device removed, in accordance with an embodiment.
Figure 21B:
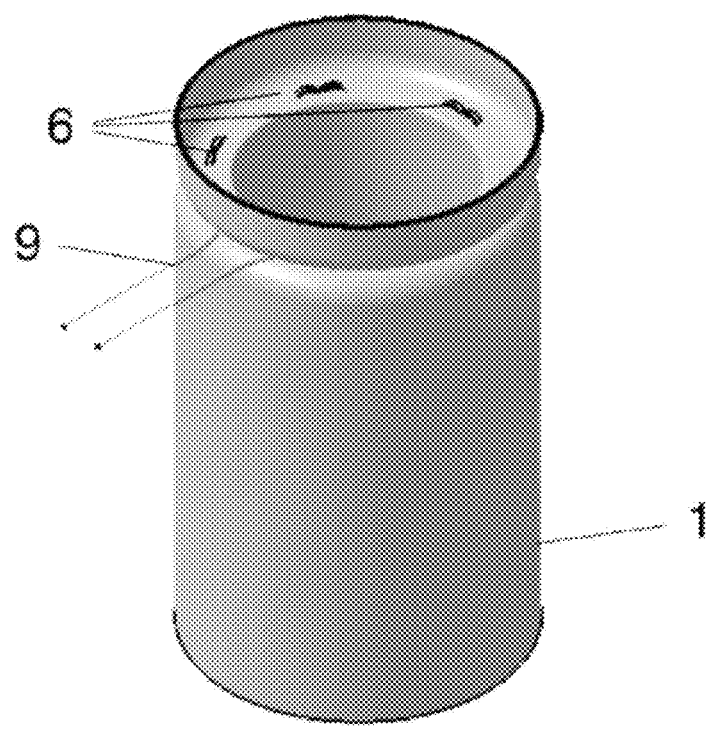
Figure 21C:
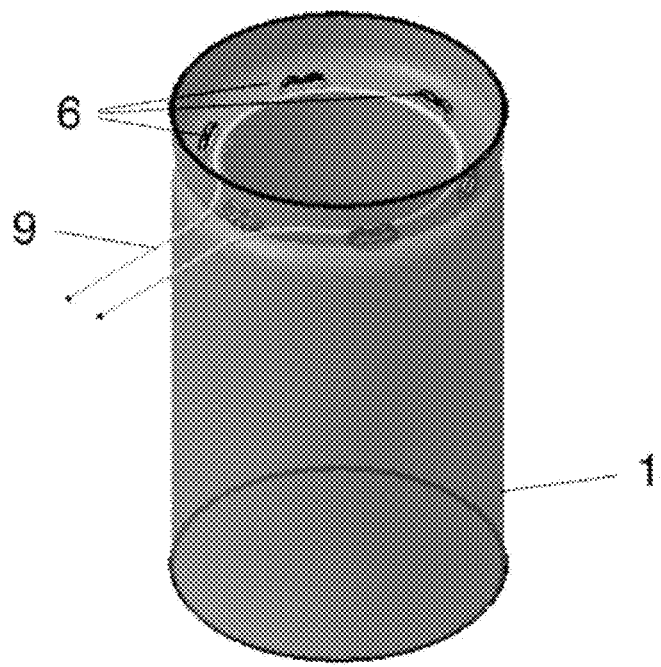
FIG. 21c shows the hollow viscus transparent.
Figure 22:
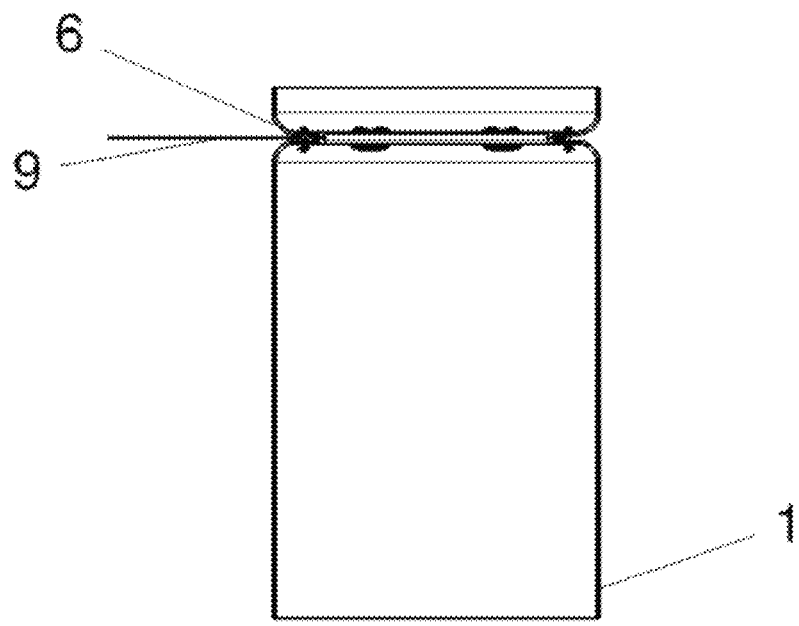
FIG. 22 is a cross-sectional view of the hollow viscus of FIGS. 21a-21c.
Figure 23:
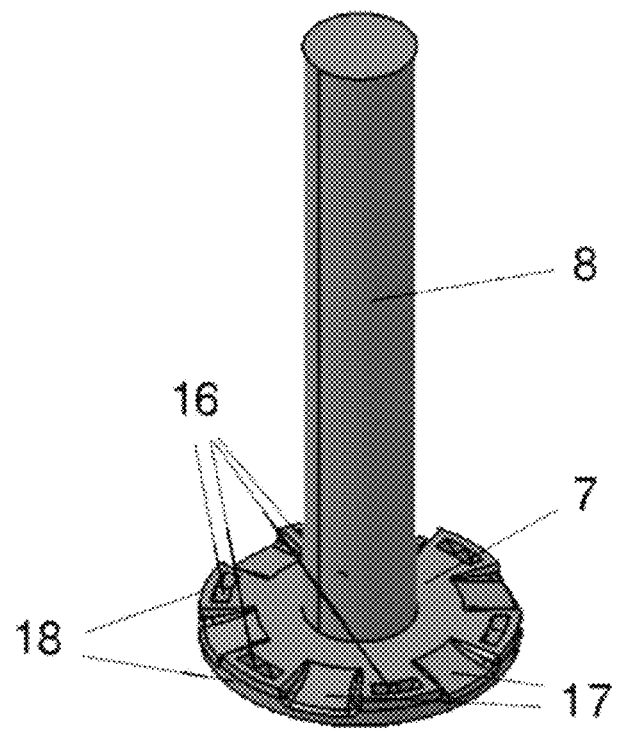
FIG. 23 shows an embodiment of an anvil illustrating the grooves.

In accordance with an embodiment illustrated in FIGS. 19a-20, a second method is used to remove the device from the hollow viscus if the suturing thread 9 was not knotted but only pushed (by pushing stick 10). Specifically, the pursing region 12 of the hollow viscus 1 is opened to allow the passage of contents along the hollow viscus 1. The suturing thread 9 is loosened, and the anvil 7 is pulled back with the stapler through the folded pursing region 12 of the hollow viscus 1, as shown in FIGS. 19a-20. The tubular case 3 is then removed from the hollow viscus 1, leaving the hollow viscus 1 with the suturing thread 9 loose but secured in place by the staples 6. This allows the pursing region 12 to be subsequently opened or closed as necessary, for example, in order to remove a tumorous colon through the anus thus avoiding an additional incision in the abdomen. Subsequently, in a manner similar to the first method discussed above, the suturing thread 9 may be tightened and knotted around the pole of a conventional circular stapler, and the blade of the conventional circular stapler may be used to break the pursing region 12 containing the staples 6 and the suturing thread 9, so that they may be removed after the anastomosis has been performed.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for purse-suturing a hollow viscus comprising a purse-suturing device for suturing a hollow viscus, the device comprising: a circular stapler comprising: a tubular case configured to be inserted inside a portion of a hollow viscus; a tubular stapler head disposed in a first interior of the tubular case and configured to be displaced concentrically along the interior of the tubular case and to push staples, comprising a staple carrier; and an anvil against which staples are folded, the anvil having a pole configured to be displaced concentrically along a second interior of the tubular stapler head; and a suturing thread configured to be wound around the hollow viscus and tightened around a selected section of a wall of the hollow viscus; wherein: the pole of the anvil is configured to be displaced between a pursing position in which the anvil is retracted a selected distance from the stapler head, defining a space between the anvil and the stapler head and an associated section of the wall of the hollow viscus around which the suturing thread is wound, and a stapling position in which the anvil is proximate the stapler head, compressing and folding the section of the wall of the hollow viscus, the method comprising:

introducing the tubular stapler head of the circular stapler through the lumen of the hollow viscus until the tubular stapler head is placed in a position such that the anvil is spaced apart from the staple carrier in the pursing position;

placing the suturing thread around the viscus and tightening against the pole of the anvil thereby creating a pursing region of the wall of the hollow viscus between the staple carrier of the stapler head and the anvil;

displacing the pole of the anvil concentrically along the interior of the stapler head to the stapling position, wherein the pursing region of the wall of the hollow viscus is compressed and folded between the anvil and the staple carrier of the stapler head, thereby driving the staples out of the staple carrier and folded by the anvil;

cutting the hollow viscus at a level of the anvil or the stapler head to form the hollow viscus with a purse suture at the end thereof;

retracting the pole of the stapler head to the pursing position, releasing the wall of the hollow viscus and allowing the removal of the device, wherein the suturing thread is tightened with a pushing stick by inserting a first and second ends of the suturing thread into the pushing stick such that the pushing stick contacts the staple carrier to fasten the suturing thread around the hollow viscus and the pole.

2. The method according to claim 1, wherein the pushing stick contacts the staple carrier through spaces provided by alternate bevel inclined slots and anvil projections in the anvil.

3. The method according to claim 1, wherein the pursing region of the hollow viscus is opened to allow the passage of contents along the hollow viscus, the suturing thread is loosened and the anvil is pulled back with the stapler through the pursing region of the hollow viscus, then the tubular case is removed from the hollow viscus leaving the hollow viscus with the suturing thread loose but secured in place by the staple.

* * * * *